United States Patent [19]
Moriconi et al.

[11] 4,269,364
[45] May 26, 1981

[54] NEEDLE CHOPPER APPARATUS

[76] Inventors: Dario J. Moriconi, 6916 Old Kings Rd., Apt. 24, Jacksonville, Fla. 32217; John G. Elder, 6602 Barkwood Dr., Jacksonville, Fla. 32211

[21] Appl. No.: 2,990

[22] Filed: Jan. 12, 1979

[51] Int. Cl.³ .................................................. B02C 13/31
[52] U.S. Cl. .............................................. 241/36; 241/99; 241/100; 241/224; 241/285 A
[58] Field of Search ............... 241/36, 99, 100, 221, 241/222, 285 R, 285 A, 186 R, 189 R, 224

[56] References Cited

U.S. PATENT DOCUMENTS

| | | | |
|---|---|---|---|
| 1,333,094 | 3/1920 | Reed | 241/36 X |
| 1,706,643 | 3/1929 | Wiley | 241/99 X |
| 2,205,898 | 6/1940 | Chandler | 241/36 X |
| 2,620,988 | 12/1952 | Tellier | 241/99 X |
| 3,010,662 | 11/1961 | Johnson | 241/36 |
| 3,750,966 | 8/1973 | Anderson | 241/99 |
| 3,764,080 | 10/1973 | Wagner | 241/186 R |
| 3,926,379 | 12/1975 | Dryden et al. | 241/99 X |
| 3,929,295 | 12/1975 | Montalbano | 241/99 X |

Primary Examiner—Mark Rosenbaum
Attorney, Agent, or Firm—McGlynn and Milton

[57] ABSTRACT

A needle chopper apparatus having a rotor with radially extending blades disposed in and along the longitudinal axis of a tube member. While rotating, the blades are in immediate proximity to an inner smooth cylindrical surface of the tube member. A feed chute extends into an inlet of the tube member where the blades react with the edge of the inlet to chop disposable items into particles. The particles go through an outlet in the tube member to a container that holds a disinfectant which is circulated to the feed chute and into the tube while the items are being chopped. One end of the tube is sealed by an annular plug and the other end extends from the top portion of a mounting panel. A housing is formed by an outer cabinet that is slid over an inner cabinet and coupled together by inwardly turned tabs on the outer cabinet. The mounting panel divides the housing into a front compartment and a back compartment. The mounting panel has a top portion offset in a vertical plane from a bottom portion by a horizontally extending intermediate portion such that the bottom portion defines an enlarged area in the front compartment to receive the container. A probe responsive to liquid levels extends into the container and is operatively connected to a sensor disposed in the power circuit to an electric motor. Control components and a timing means are disposed in the rear compartment with the electric motor to prevent operation of the apparatus under certain conditions.

28 Claims, 5 Drawing Figures

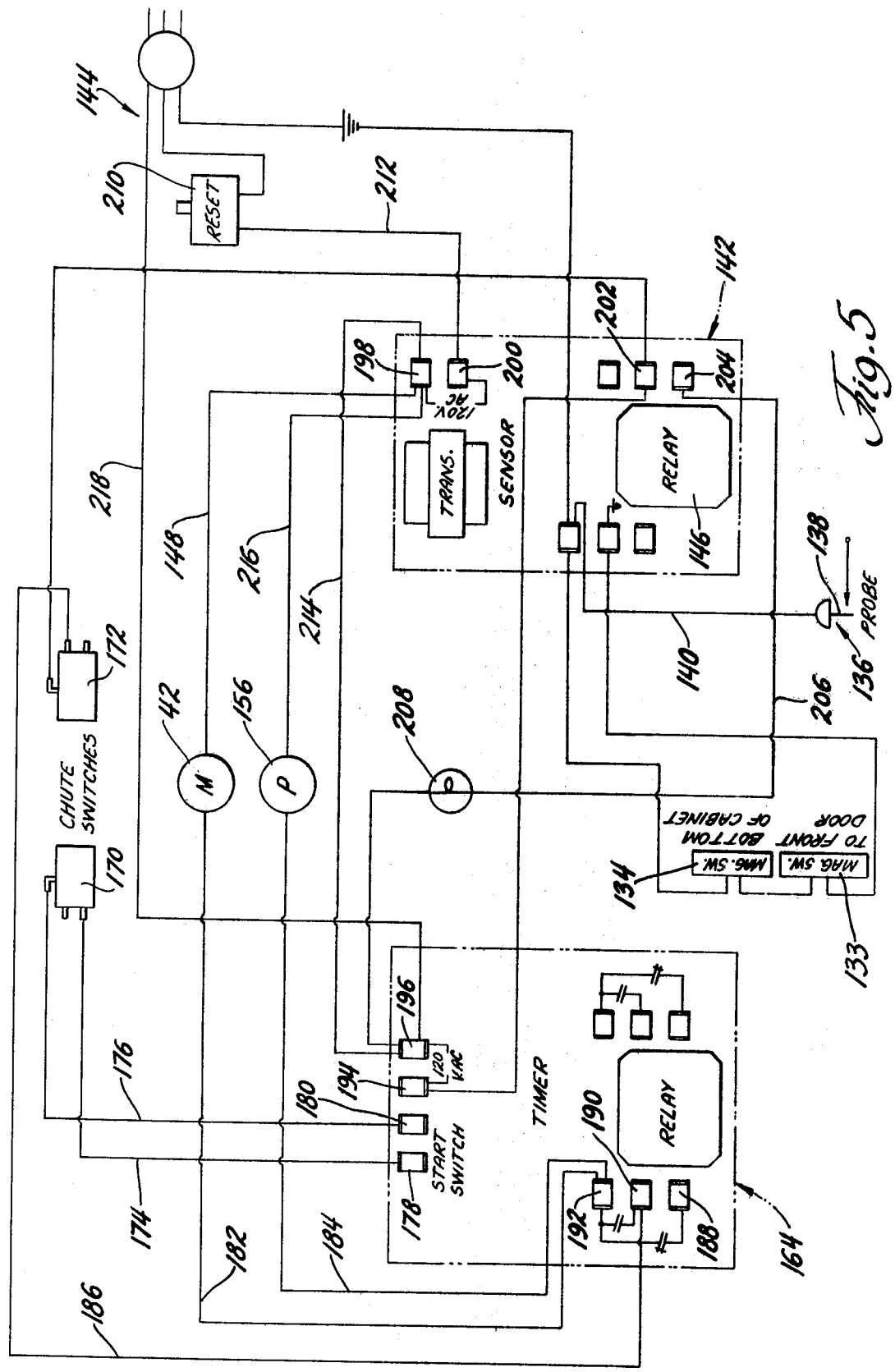

NEEDLE CHOPPER APPARATUS

BACKGROUND OF THE INVENTION (1) Field of the Invention

The subject invention relates to an improved needle chopper apparatus for the safe and convenient disposal of needles, syringes and the like that are used in various health care facilities such as hospitals, doctor's offices, clinics, etc. An outstanding and difficult problem exists in disposing of disposable items used in the medical field. These items must be disposed of, disinfected and rendered harmless in order to prevent the transmission of diseases, to avoid accessibility of used needles and syringes by unauthorized persons, and for other normal reasons of sanitation. Thus, a need has arisen to assure a safe and convenient way of disposing of disposable medical items.

(2) Description of the Prior Art

Typically, the prior art waste disposal devices include a feed chute, destructing means and particle collecting means positioned to receive particles resulting from the destruction operation. The prior art devices, however, have not provided an acceptable solution to the problem of safely and conveniently disposing of disposable items.

SUMMARY OF THE INVENTION

The subject invention relates to an improved needle chopper apparatus comprising a feed chute for receiving disposable items and a chopper means for chopping disposable items into particles. A tube member has a cylindrical configuration and terminates in a first end and a second end opposite therefrom. The chopper means is rotatably disposed in and along the longitudinal axis of the tube member. An inlet and an outlet defined by the tube member allow disposable items into and out of the tube member. Reaction means on the edge of the inlet react with the chopper means to chop the disposable items and collecting means collect the particles from the outlet.

PRIOR ART STATEMENT

Typical of a disposable item destruction apparatus of the type to which the instant invention pertains is that shown in U.S. Pat. No. 3,926,379 granted to G. E. Dryden et al. on Dec. 16, 1975. This patent discloses a destruction apparatus employing a hammer mill to destroy disposable items and has a liquid disinfectant reservoir which supplies disinfectant to a pump which discharges it into the hammer mill from which it descends into a collecting bag which has apertures to allow the disinfectant to return to the reservoir. This patent does not, however, disclose a chopper means being rotatably disposed in a tube member along the longitudinal axis of the tube member.

U.S. Pat. No. 1,706,643 granted on Mar. 26, 1929 to S. W. Wiley discloses a laboratory mill having a rotary cutter disposed in a cylindrical housing. The blades disclosed in this patent, however, react with a plurality of blades which are mounted in and extend from the cylindrical housing.

U.S. Pat. No. 3,764,080 granted on Oct. 9, 1973 to M. Wagner discloses a waste disposal device for plastic wastes of endless dimensions such as pipes, rods and the like. This patent does not, however, suggest a chopper rotatably disposed in a tube member having a cylindrical configuration.

Thus, none of these patents discloses an improved needle chopper apparatus having a chopper rotatably disposed along the longitudinal axis of a tube member with reaction means on the edge of an inlet in the tube member to react with the chopper means to chop disposable items. Additionally, none of the patents discussed above disclose the specific structure set forth hereinafter of a housing that is divided into front and rear compartments by a novel mounting panel and various control and safety features.

BRIEF DESCRIPTION OF THE DRAWINGS

Other advantages of the present invention will be readily appreciated as the same becomes better understood by reference to the following detailed description when considered in connection with the accompanying drawings wherein:

FIG. 5 is a schematic diagram of the circuit for a needle chopper apparatus constructed in accordance with the instant invention.

DESCRIPTION OF THE PREFERRED EMBODIMENT

Figure 1:
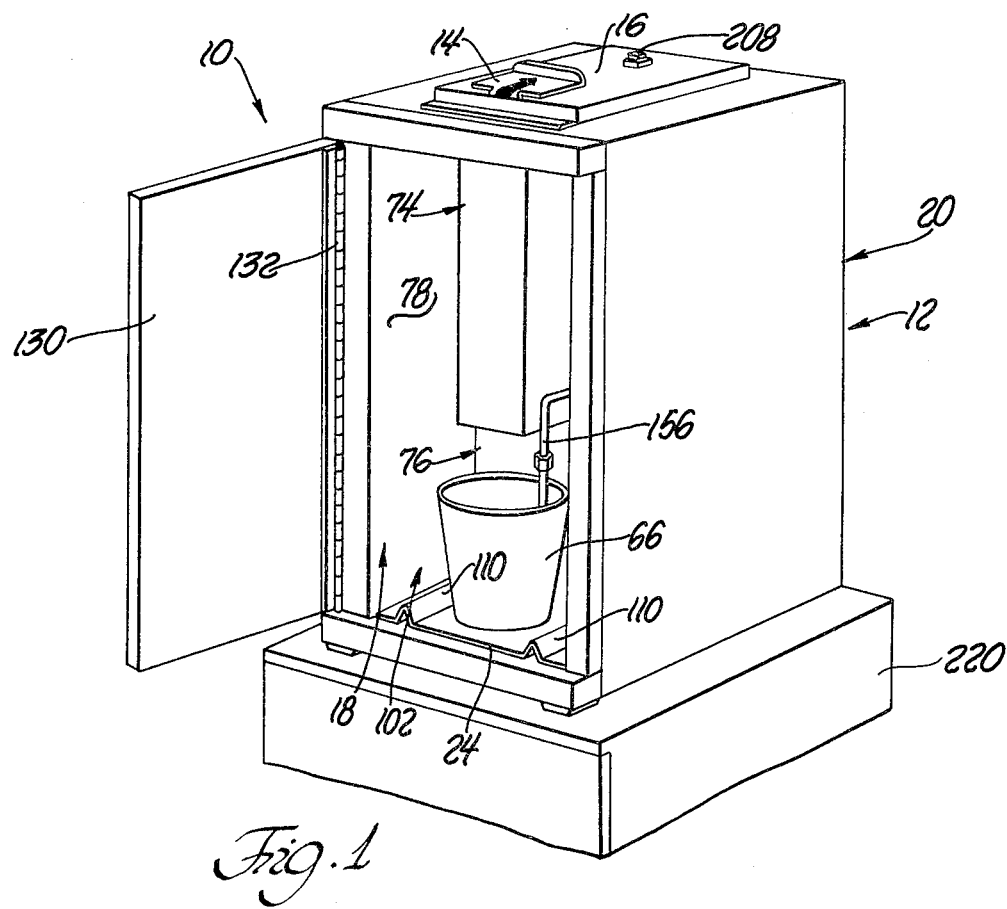
FIG. 1 is a perspective view of a needle chopper apparatus constructed in accordance with the instant invention.

Referring to FIG. 1, a needle chopper apparatus constructed in accordance with the instant invention is generally shown at 10. A housing is generally shown at 12 and a feed door 14 is supported by the top of the housing 12 and is slidably mounted on a support plate 16 for movement between open and closed positions.

Figure 2:
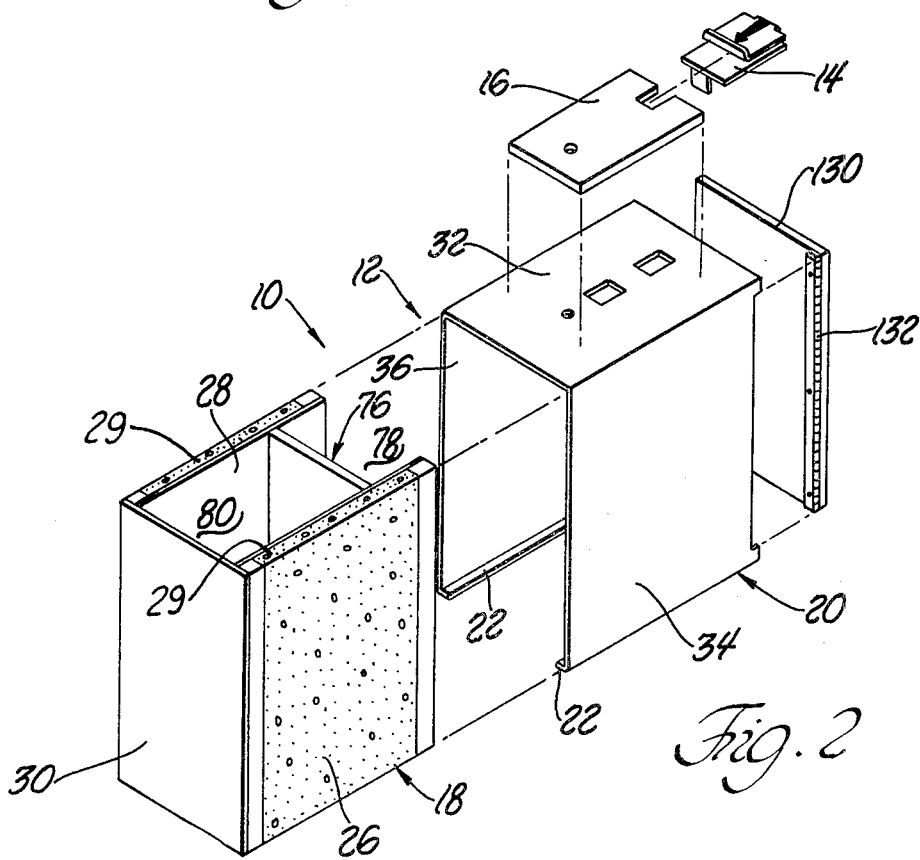
FIG. 2 is an exploded perspective view of the housing components of the apparatus shown in FIG. 1.

Referring to FIGS. 1 and 2, the housing 12 includes an inner cabinet generally indicated at 18 and an outer cabinet generally indicated at 20. The inner cabinet 18 is of smaller size than the outer cabinet 20 whereby the outer cabinet 20 may be slid over the inner cabinet 18. Coupling means for coupling the cabinets together are provided by inwardly turned tabs 22 on the bottom of outer cabinet 20 which engage with the inner cabinet 18. The inner cabinet 18 includes a base 24, two side walls 26 and 28, and a back wall 30 extending from the base 24. The outer cabinet 20 has a top wall 32 and two side walls 34 and 36 extending downwardly from the top wall 32. Additionally, the housing 12 includes insulation 29 for reducing noise levels during operation.

Figure 3:
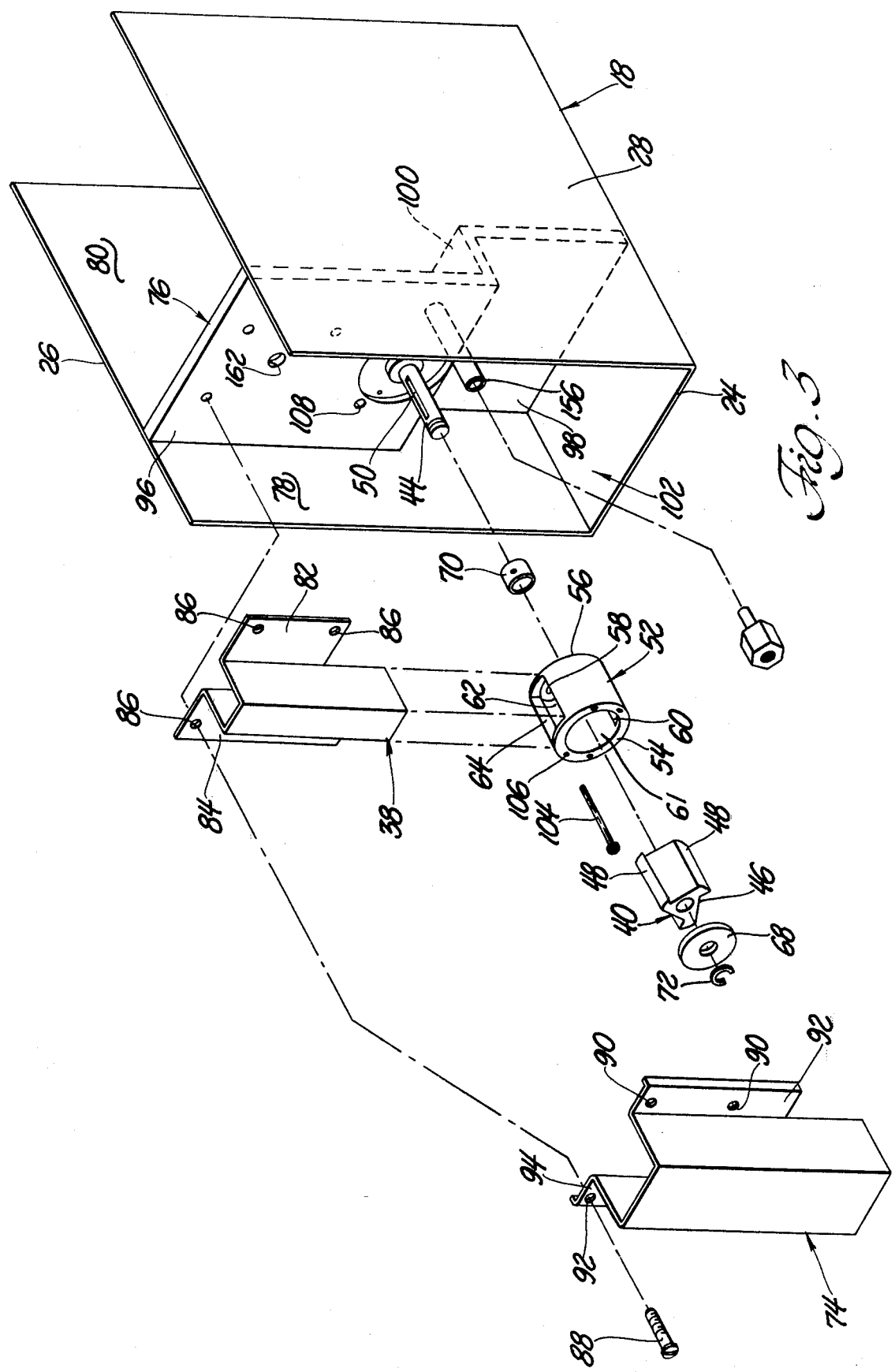
FIG. 3 is an exploded perspective view showing inside components in the front of the apparatus shown in FIG. 1.

A feed chute generally indicated at 38 receives disposable items such as needles, syringes and the like. The feed door 14 allows access to the feed chute 38 in its open position and prevents access to the feed chute 38 when the feed door 14 is in its closed position. The feed chute 38 delivers disposable items to a chopper means generally indicated at 40 for chopping the disposable items into particles. A drive means for rotating the chopper means 40 is generally indicated at 42 in FIG. 4. As shown in FIG. 3, a drive shaft 44 extends from the drive means 42. The chopper means 40 includes a rotor portion 46 mounted on the drive shaft 44 and has blades 48 extending radially therefrom. The chopper means 40 is rotated by the drive shaft 40 by a keyway 50 or the like.

Still referring to FIG. 3, the chopper means 40 is disposed in a tube member generally indicated at 52. The tube member 52 has a cylindrical configuration and terminates in a first end 54 and a second end 56 opposite therefrom. The chopper means 40 is disposed in the tube member 52 along the longitudinal axis of the tube member 52 and is rotatable therein. The tube member 52 defines an inlet 58 and an outlet 60 to allow disposable items into and out of the tube member 52. The tube member 52 has an inner smooth cylindrical surface 61 and the chopper means 40 is in immediate proximity to the smooth cylindrical surface 61 while rotating relative thereto. Reaction means on the edge of the inlet 58 react with the chopper means 40 to chop disposable items. The reaction means is provided by the edges 62 and 64 of the portion of the tube member 52 defining the inlet 58. The edges 62 and 64 may include carbide strips and the tips of the blades 48 may also be made of carbide in order to improve cutting and wear characteristics. It is important that there is very little clearance between the inner surface of the tube member 52 and the extremities of the blades 48 in order to obtain the desired destruction. After disposable items are chopped into particles, the particles are collected from the outlet 60 by a collecting means 66.

The feed chute 38 extends into the inlet 58 of the tube member 52 and sealing means seal the first end of the tube member 52. Thus, a liquid disinfectant or germicide may be circulated to the feed chute 38 which then goes into the tube member 52 to allow decontamination during the chopping operation.

The first end 54 of the tube member 52 is open and the sealing means includes an annular plug member 68 engaging the inner cylindrical surface 61 of the tube member 52 to close the first open end 54. The chopper means 40 is mounted on the drive shaft 44 and has a shaft collar 70 at one end and is assembled and held in place with a snap ring 72 at the other end. The sealing means also includes a cover member 74 covering the feed chute 38 and the first end 54 of the tube member 52.

Referring to FIGS. 1 through 4, a mounting panel generally indicated at 76 divides the housing 12 into a front compartment 78 and a rear compartment 80. The tube member 52 is supported by the mounting panel 76 at the second end 56 of the tube member 52 and extends into the front compartment 78. More specifically, the feed chute 38 has a U-shaped cross section and has flanges 82 and 84 for mounting the feed chute 38 to the mounting panel 76 in the front compartment 78. The flanges 82 and 84 of the feed chute 38 have holes 86 which receive screws 88 which also extend through holes 90 in flanges 92 and 94 of the cover member 74. The mounting panel 76 extends between and is connected to the side walls 26 and 28 of the inner cabinet 18.

Figure 4:
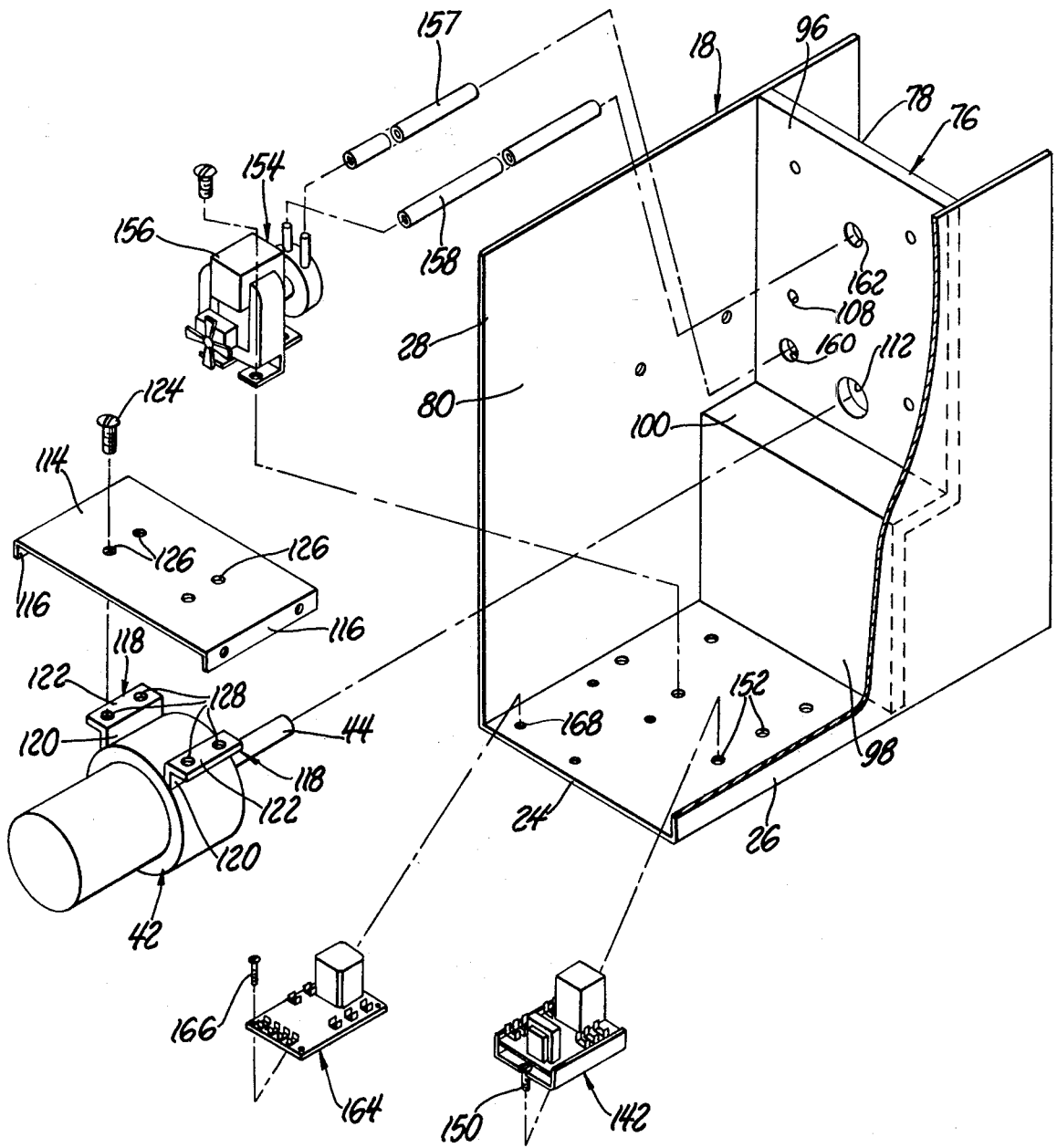
FIG. 4 is an exploded perspective view partially broken away and in cross section showing the inside components in the rear of the apparatus shown in FIG. 1.

As best seen in FIGS. 3 and 4, the mounting panel 76 includes a top portion 96 and a bottom portion 98 and an intermediate portion 100 therebetween. The intermediate portion 100 extends in a plane transverse to the plane of the top portion 96 and the bottom portion 98 to provide an enlarged area generally indicated at 102 of the front compartment 78 under the intermediate portion 100 for receiving the collecting means 66. In other words, the top portion 96 and bottom portion 98 are in offset vertical planes with the intermediate portion 100 extending horizontally between the top portion 96 and the bottom portion 98. The bottom portion 98 is offset rearwardly of the top portion 96 to define the enlarged area 102 of the front compartment 78. The tube member 52 is attached to the top portion 96 of the mounting panel 76 by screws 104 which extend through suitable openings 106 in the tube member 52 and are received by suitable openings 108 in the top portion 96 of the mounting panel 76. Thus, the tube member 52 extends forwardly from the top portion 96 of the mounting panel 76 with its outlet 60 disposed above and directed downwardly to the enlarged area 102.

Referring to FIG. 1, the collecting means 66 is guided by guide means to a collecting position in the front compartment 78 and beneath the outlet 60 of the tube member 52 whereby the particles fall into the collecting means 66 after being chopped by the chopper means 40. The guide means includes channels 110 on the bottom or base 24 of the inner cabinet 18 of the housing 12 in the front compartment 78.

The drive means 42 is disposed in the rear compartment 80 with the drive shaft 44 extending through an opening 112 in the top portion 96 of the mounting panel 76 and is connected to the chopper means 40 as described above. Additionally, control components are disposed in the rear compartment 80 and are more specifically described hereinafter. Support means support the drive means 42 in the rear compartment 80 adjacent the top portion 96 of the mounting panel 76. As shown in FIG. 4, the support means includes a plate member 114 having mounting tabs 116 attached to the side walls 26 and 28 of the inner cabinet 18. The drive means 42 has a cylindrical configuration and includes L-shaped brackets generally indicated at 118 having one leg 120 of each bracket 118 attached to the drive means 42 and the other leg 122 attached to the plate 114 by screws 124 extending through suitable holes 126 in the plate members 114 and holes 128 in the legs 122 of the mounting tabs 118. The drive means 42 is an electic motor.

Referring to FIGS. 1 and 4, the collection means 66 includes a container that is impervious to liquid for containing a liquid decontaminant or germicide. An access door 130 is supported by the front compartment 78 or, more specifically, the access door 130 is hingedly mounted at 132 to the outer cabinet 20. The access door 130 is movable between open and closed positions to allow access to the collection means or container 66.

Shutoff means are provided to allow operation of the drive means 42 to rotate the chopper means 40 only when the collecting means or container 66 is in its collecting position provided by the channels 110 as described above. The shutoff means includes a magnet in the collection means 66 and a switch shown at 134 in FIG. 5 disposed in the front compartment 78 which is responsive to the magnet. In other words, if the collecting means 66 is not in its collecting position under the outlet 60 of the tube member 52, then the apparatus 10 will be inoperative.

Additionally, signal means provide a signal when the collection means 66 is full. The signal means includes a conductive probe 136 which is responsive to the level of liquid in the container 66 in order to prevent operation of the drive means 42 to rotate the chopper means 40 when the liquid reaches a predetermined level in the container 66. The conductive probe 136 may be in the form of a wire 138 which is operatively connected by lead 140 to a sensing means generally indicated at 142 disposed in the power circuit generally shown at 144 to the electric motor 42. The sensing means 142 may be a solid state resistance sensor having a transformer and suitable switches therein and including a relay 146 which opens the circuit to the electric motor 42 in response to temperature or liquid. In other words, no current can flow through lead 148 when the liquid in the container 66 reaches a certain level. Thus, when the container 66 is full of chopped particles, the container 66 must be replaced before the apparatus 10 is again operative. As shown in FIG. 4, the sensing means 142 which provides the automatic shutoff is positioned in the rear compartment 80 by suitable bolts 150 which are received by holes 152 in the base 24 of the inner cabinet 18.

Circulating means generally shown at 154 circulates the liquid decontaminant from the collecting means 66 to the feed chute 38 thereby allowing the liquid decontaminant to flow into the tube member 52 to decontaminate the tube member 52 and the chopper means 40. In other words, the disposable items are decontaminated while they are being chopped into particles. The circulating means 154 includes pump means 156 for pumping the liquid, intake means 157 for taking the liquid from the collecting means 66 and output means 158 for dispensing the liquid to the feed chute 38. The intake means 157 and the output means 158 may take the form of plastic tubing. The pump means 156 is positioned in the rear compartment 80 and the intake means 157 extends through an opening 160 and the output means 158 extends through an opening 162, both openings 160 and 162 being in the top portion 96 of the mounting panel 76.

Turning now to the remainder of the control components mentioned above and referring to FIGS. 4 and 5, timing means generally indicated at 164 operate the drive means or electric motor 42 to operate the chopping means 40 for a predetermined time period after the feed door 14 is moved to its closed position. The timing means 164 may be a solid state transistorized timer which is positioned in the rear compartment 80 and attached by suitable screws 166 received by holes 168 in the base 24 of the inner cabinet 18. Control means are also provided which are responsive to the access door 130 and the feed door 14 for allowing operation of the drive means 42 only when the access door 130 and the feed door 14 are in their respective closed positions.

The access door 130 includes a magnet to activate a magnetic reed switch 133 which is normally opened but becomes closed when the access door 130 is closed. The magnetic reed switch is positioned in the side wall 28 of the housing 12.

The feed door 14 compresses two microswitches 170 and 172 when the feed door 14 is in its closed position. Microswitch 170 is normally open and microswitch 172 is normally closed. When the feed door 14 is opened, the normally open switch 170 is closed and current then flows through leads 174 and 176 to start switches 178 and 180, respectively, of the timing means 164. This sets the timing means 164 to supply current through lead 182 to the electric motor 42 and through lead 184 to the pump means 156. In the event that the feed door 14 is opened while the machine is running, then the normally closed switch 172 is opened which cuts off the current to lead 186 which is operatively connected to switches 188, 190 and 192 which are connected in series to thereby shut off the power through leads 182 and 184 to the electric motor 42 and pump means 156, respectively.

120 volt AC switches 194 and 196 of the timing means 164 are operatively connected to 120 volt AC switches 198 and 200 and another microswitch 202 which is normally closed of the sensing means 142. Thus, the sensing means 142 acts in conjunction with the timing 164 to prevent the apparatus 10 from operating when the feed door 14 or the access door 130 are open or when the collection means 66 is not in its proper position or is full. Additionally, the sensing means 142 includes a switch 204 which is normally open but is closed when the collecting means 66 is full; i.e., when the liquid touches the probe 136 which supplies power through lead 206 to an indicator light 208 which may be positioned on top of the housing 12 to allow a user to have a visable signal that the collecting means 66 is full.

A reset switch 210 is also provided and is operatively connected by lead 212 to switch 200 which is operatively associated with switch 198. Switch 198 is connected by lead 214 to switch 196 of the timing means 164 and by lead 216 to the pump 156 and by lead 148 to the electric motor 42 to reset the machine in the event that any of the components or the chopper means 40 become jammed. In other words, lead 218 from the power source 144 is operatively connected to the timing means 164 and the reset switch 210 is disposed in the lead 212 to the sensing means 142 in order to reset the machine if necessary.

The subject invention provides a solution to the problems of disposing of disposable items. The disposable items are decontaminated and deodorized during the chopping operation and the various safety features prevent inadvertent operation during unsafe conditions. The container or collecting means 66 can be removed from the housing 12 and non-leakable covers will seal the container 66 in order to safely dispose of the destroyed items. The needle chopper apparatus 10 may be conveniently mounted on a storage cabinet 220 shown in FIG. 1 which may be used to store additional containers 66. The storage cabinet 220 may be mounted on rollers or the apparatus 10 may be installed in a self-contained portable cart.

The invention has been described in an illustrative manner, and it is to be understood that the terminology which has been used in intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

The embodiments of the invention in which an exclusive property or privilege is claimed are defined as follows:

1. A needle chopper apparatus comprising; a vertical feed chute for receiving disposable items, chopper means for chopping disposable items into particles, a tube member having a cylindrical configuration and terminating in a first end and a second end opposite therefrom, said chopper means being disposed in said tube member along the longitudinal axis of said tube member and rotatable therein, an inlet and an outlet defined by said tube member to allow disposable items to fall into and out of said tube member with said inlet having an edge, said feed chute extending to said inlet, reaction means on the edge of said inlet for reacting with said chopper means to chop and cut disposable items, and removable collecting means for collecting the falling particles from said outlet, said tube member including an inner smooth cylindrical surface which is continuous and uninterrupted completely around the interior of said tube member with all of the peripheral edges of said inlet and outlet intersecting said inner cylindrical surface, said reaction means being at the intersection of said edge of said inlet and said inner cylindrical surface and said chopper means being in immediate proximity and close clearance to said cylindrical surface while rotating relative thereto for shearing disposable items between said reaction means and said chopper means as said chopper means engages a disposable item in said inlet and forces the disposable item against said reaction means in said inlet so that the line of shearing is substantially parallel to said inner cylindrical surface.

2. An apparatus as set forth in claim 1 including sealing means for sealing said first end of said tube member.

3. An apparatus as set forth in claim 2 wherein said first end is open and said sealing means includes an annular plug member engaging said inner cylindrical surface to close said first open end.

4. An apparatus as set forth in claim 3 wherein said feed chute extends into said inlet of said tube member.

5. An apparatus as set forth in claim 4 wherein said sealing means further includes a cover member covering said feed chute and said first end of said tube member.

6. An apparatus as set forth in claim 5 including a housing and a mounting panel dividing said housing into front and rear compartments, said tube member being supported by said mounting panel at said second end of said tube member and extending into said front compartment.

7. An apparatus as set forth in claim 6 wherein said housing includes an inner cabinet and an outer cabinet, and coupling means for coupling said cabinets together.

8. An apparatus as set forth in claim 7 wherein said inner cabinet is of smaller size than said outer cabinet whereby said outer cabinet may be slid over said inner cabinet, and said coupling means includes inwardly turned tabs on said outer cabinet engaged with said inner cabinet.

9. An apparatus as set forth in claim 6 wherein said feed chute has a U-shaped cross section and includes flanges for mounting said feed chute to said mounting panel in said front compartment.

10. An apparatus as set forth in claim 6 wherein said mounting panel includes a top portion and a bottom portion and an intermediate portion therebetween, said intermediate portion extending in a plane transverse to the plane of said top portion and said bottom portion to provide an enlarged area of said front compartment under said intermediate portion for receiving said collecting means, said tube member extending from said top portion of said mounting panel with said outlet thereof disposed above and directed to said enlarged area.

11. An apparatus as set forth in claim 10 wherein said housing includes an inner cabinet having a base, two side walls and a back wall extending upward from said base, said mounting panel extending between and connected to said side walls of said inner cabinet.

12. An apparatus as set forth in claim 11 wherein said housing includes an outer cabinet having a top wall and two side walls extending downward from said top wall.

13. An apparatus as set forth in claim 10 including drive means for rotating said chopper means and support means for supporting said drive means in said rear compartment adjacent said top portion of said mounting panel.

14. An apparatus as set forth in claim 13 wherein said support means includes a plate member having mounting tabs attached to said side walls of said inner cabinet.

15. An apparatus as set forth in claim 14 wherein said drive means has a cylindrical configuration and includes L-shaped brackets having one leg of each bracket attached to said drive means and the other leg attached to said plate.

16. An apparatus as set forth in claim 13 including shut-off means for allowing operation of said drive means to rotate said chopper means only when said collecting means is in said collecting position.

17. An apparatus as set forth in claim 16 wherein said shut-off means includes a magnet in said collection means and a switch disposed in said front compartment responsive to said magnet.

18. An apparatus as set forth in claim 17 including signal means for providing a signal when said collection means is full.

19. An apparatus as set forth in claim 18 wherein said collection means includes a container impervious to liquid for containing a liquid decontaminant and said signal means includes a conductive probe responsive to the level of liquid in said container for preventing operation of said drive means to rotate said chopper means when the liquid reaches a predetermined level in said container.

20. An apparatus as set forth in claim 19 wherein said drive means includes an electric motor and wherein said conductive probe includes a wire operatively connected to a sensing means disposed in the power circuit to said electric motor.

21. An apparatus as set forth in claim 20 including a feed door supported by the top of said housing for movement between open and closed positions for allowing access to said feed chute in said open position and for preventing access to said feed chute in said closed position, timing means for operating said drive means to rotate said chopping means for a predetermined time period after said feed door is moved to said closed position, an access door movable between open and closed positions supported by said front compartment of said housing for allowing access to said collection means, and control means responsive to said access door and said feed door for allowing operation of said drive means only when said access door and said feed door are in their respective closed positions.

22. An apparatus as set forth in claim 21 wherein said drive means includes a drive shaft extending through said top portion of said mounting panel and into said front compartment, said chopper means including a rotor portion mounted on said drive shaft and having blades extending radially therefrom.

23. An apparatus as set forth in claim 22 wherein said housing includes insulation for reducing noise levels.

24. An apparatus as set forth in claim 10 including guide means for guiding said collecting means to a collecting position in said front compartment and beneath said outlet of said tube member whereby the particles fall into said collecting means after being chopped by said chopper means.

25. An apparatus as set forth in claim 24 wherein said guide means includes channels on the bottom of said housing in said front compartment.

26. An apparatus as set forth in claim 1 including circulating means for circulating liquid decontaminant from said collecting means to said feed chute thereby allowing the liquid decontaminant to flow into said tube member to decontaminate said tube member and said chopper means.

27. An apparatus as set forth in claim 26 wherein said circulating means includes pump means for pumping the liquid, intake means for taking liquid from said collecting means and output means for dispensing the liquid to said feed chute.

28. An apparatus as set forth in claim 1 including a housing and a mounting panel dividing said housing into front and rear compartments, said mounting panel having a top portion and a bottom portion and an intermediate portion therebetween, said top and bottom portions being in offset vertical planes with said intermediate portion extending horizontally between said top and bottom portions, said bottom portion being offset rearwardly of said top portion to define an enlarged area of said front compartment, said tube member extending forwardly of said top portion with said outlet thereof directed downwardly toward said enlarged area, and drive means disposed in said rear compartment with a drive shaft extending through said top portion and connected to said chopper means, and control components disposed in said rear compartment.

* * * * *